(12) United States Patent
Stroud (10) Patent No.: US 9,433,484 B2
(45) Date of Patent: Sep. 6, 2016

(54) ARTIFICIAL BREEDING TECHNIQUES FOR BOVINES INCLUDING SEMEN DILUENTS AND AI APPARATUS

(76) Inventor: Brad K. Stroud, Weatherford, TX (US)

( * ) Notice: Subject to any disclaimer, the term of this patent is extended or adjusted under 35 U.S.C. 154(b) by 1099 days.

(21) Appl. No.: 12/506,723

(22) Filed: Jul. 21, 2009

(65) Prior Publication Data

US 2009/0281371 A1   Nov. 12, 2009

Related U.S. Application Data

(63) Continuation-in-part of application No. 11/829,240, filed on Jul. 27, 2007, now Pat. No. 8,202,210.

(51) Int. Cl.
*A61D 19/02* (2006.01)
*A61M 25/00* (2006.01)
*A61M 31/00* (2006.01)

(52) U.S. Cl.
CPC ............ *A61D 19/027* (2013.01); *A61M 25/00* (2013.01); *A61M 31/00* (2013.01)

(58) Field of Classification Search
CPC .... A61B 17/42; A61B 17/425; A61B 17/43; A61B 17/435; A61M 31/00; A61M 3/02; A61M 3/025; A61M 3/0262; A61M 3/0279; A61M 2210/10; A61M 2210/1017; A61M 2210/1021; A61M 2210/1425; A61M 2210/1433; B01L 3/021; B01L 3/0217; B01L 3/022; B01L 3/0231
USPC ........ 600/33–35; 604/27, 28, 36–38, 48, 73, 604/164.01, 164.13, 181, 500, 514, 515
See application file for complete search history.

(56) References Cited

U.S. PATENT DOCUMENTS

| | | | |
|---|---|---|---|
| 2,566,632 A | | 9/1951 | Propp |
| 2,944,541 A | * | 7/1960 | Sacchi et al. .................. 600/35 |
| 3,256,884 A | | 6/1966 | Hill et al. |
| 3,811,423 A | | 5/1974 | Dickinson, III et al. |
| 3,811,443 A | | 5/1974 | Dickinson, III et al. |
| 3,877,430 A | | 4/1975 | Wieder |

(Continued)

FOREIGN PATENT DOCUMENTS

| | | |
|---|---|---|
| CA | 1073286 | 3/1980 |
| EP | 0071538 | 9/1983 |

(Continued)

OTHER PUBLICATIONS

Amann, Rupert P., Exposure of Thawed Frozen Bull Sperm to a Synthetic Peptide Before Artificial Insemination Increases Fertility, Journal of Andrology, (1999), 42-46, vol. 20, No. 1.

(Continued)

*Primary Examiner* — Charles A Marmor, II
*Assistant Examiner* — Carrie R Dorna
(74) *Attorney, Agent, or Firm* — Husch Blackwell LLP (57) ABSTRACT

In the preferred embodiment, bovine semen is mixed with a "suitable solution" to form an insemination medium which is injected into the reproductive organs of a female bovine to flood the uterine horns in a nonsurgical AI procedure. The invention includes an AI instrument having a disposable, single use pipette that may be used with this nonsurgical procedure. The AI instrument does not include a balloon and is referred to as "catheter free". Preferably, the uterine horns are flooded concurrently, but in the alternative, they may be flooded sequentially.

11 Claims, 5 Drawing Sheets

(56) References Cited

U.S. PATENT DOCUMENTS

| | | | |
|---|---|---|---|
| 3,889,676 | A | 6/1975 | Greene |
| 3,910,275 | A | 10/1975 | Babey et al. |
| 4,301,797 | A | 11/1981 | Pollack |
| 4,305,392 | A | 12/1981 | Chester |
| 4,324,235 | A | 4/1982 | Beran |
| 4,335,723 | A | 6/1982 | Patel |
| 4,419,986 | A | 12/1983 | Leibo |
| 4,457,313 | A | 7/1984 | Alter |
| 4,493,700 | A | 1/1985 | Cassou et al. |
| 4,654,025 | A | 3/1987 | Casson et al. |
| 4,790,814 | A * | 12/1988 | Fischl et al. .................. 600/35 |
| 5,030,202 | A | 7/1991 | Harris |
| 5,147,299 | A | 9/1992 | Mendoza et al. |
| 5,147,315 | A * | 9/1992 | Weber .................. 604/164.09 |
| 5,496,272 | A | 3/1996 | Chung et al. |
| 5,674,178 | A * | 10/1997 | Root .......................... 600/35 |
| 5,899,848 | A * | 5/1999 | Haubrich .................... 600/35 |
| 5,904,665 | A | 5/1999 | Muharib |
| 5,916,144 | A | 6/1999 | Li et al. |
| 5,985,538 | A | 11/1999 | Stachecki |
| 6,071,231 | A | 6/2000 | Mendoza et al. |
| 6,130,034 | A | 10/2000 | Aitken |
| 6,140,121 | A | 10/2000 | Ellington et al. |
| 6,368,786 | B1 | 4/2002 | Saint-Ramon et al. |
| 6,454,756 | B1 | 9/2002 | Sasaki |
| 6,551,236 | B1 | 4/2003 | Liegois |
| 6,569,118 | B2 * | 5/2003 | Johnson et al. ......... 604/164.04 |
| 6,706,026 | B1 * | 3/2004 | Goldstein et al. ............ 604/278 |
| 7,056,279 | B2 | 6/2006 | Verberckmoes et al. |
| 7,339,090 | B2 | 3/2008 | Christmann |
| 2002/0038113 | A1 | 3/2002 | Gourley et al. |
| 2002/0072650 | A1 | 6/2002 | Garcia et al. |
| 2002/0156420 | A1 * | 10/2002 | Anderson ........... A61M 3/0279 604/113 |
| 2003/0008918 | A1 | 1/2003 | Kurogi et al. |
| 2003/0196213 | A1 | 10/2003 | Matthijs-Rijsenbilt et al. |
| 2004/0031071 | A1 | 2/2004 | Morris et al. |
| 2004/0199044 | A1 | 10/2004 | Verberckmoes et al. |
| 2004/0261799 | A1 | 12/2004 | Mock |
| 2005/0064579 | A1 | 3/2005 | Loskutoff et al. |
| 2005/0214733 | A1 | 9/2005 | Graham et al. |
| 2006/0079731 | A1 * | 4/2006 | Chen .......................... 600/35 |
| 2007/0255091 | A1 | 11/2007 | Ainley |
| 2009/0023980 | A1 | 1/2009 | Ainley, Jr. |
| 2009/0030268 | A1 | 1/2009 | Stroud |

FOREIGN PATENT DOCUMENTS

| | | |
|---|---|---|
| EP | 214043 | 3/1987 |
| EP | 0538786 | 4/1993 |
| EP | 0685556 | 6/1995 |
| EP | 1066802 | 8/2006 |
| FR | 2647668 | 12/1990 |
| FR | 2720407 | 12/1995 |
| GB | 867274 | 5/1964 |
| GB | 1488397 | 10/1977 |
| GB | 2031456 | 4/1980 |
| JP | 2001017026 A | 1/2001 |
| JP | 2006198158 A | 8/2006 |
| WO | 9103935 | 4/1991 |
| WO | 9428810 | 12/1994 |

OTHER PUBLICATIONS

Barth, AD, Factors Affecting Fertility with Artificial Insemination, Vet. Clin. North Am. Food Anim. Pract. (1993), 275-89, 9(2).

Berber, et al., Comparison of Two Ovsynch Protocols (Gnrh Versus LH) for Fixed Timed Insemination in Buffalo (Bubalus Bubalis), Theriogenology (2002), 1421-30, 57(5).

Bergqvist, Ann-Sofi, et al, Sulphated Glycosaminoglycans (S-GAGs) and Syndecans in the Bovine Oviduct, Animal Reproduction Science 93, (2006) 46-60.

Betteridge, K.J., An Historical Look at Embryo Trnasfer, J. Reprod. Fert., (1981), 62, 1-13.

Block, J., et al., Effect of Addition of Hyaluronan to Embryo Culture Medium on Survival of Bovine Embryos in Vitro Following Vitrification and Establishment of Pregnancy After Trasnfer to Recipients, Theriogenology, (2009), on-line publication of 9 pages.

Brackett, Benjamin G., Fertilization and Early Development of Cow Ova, Biology of Reproduction 23 (1980), 189-205.

Dairy Herd Staff, Reproductive Efficiency = Environmental Efficiency, Dairy Herd Management, (2009).

Dalton et al., Effect of a Deep Uterine Insemination on Spermatozoal Accessibility to the Ovum in Cattle: A Competitive Insemination Study, Theriogenology (1999), 883-890, vol. 51, Iss. 5.

Dalton, Jospeh C., Factors Important to the Efficiency of Artificial Insemination in Single-Ovulating and Superovulated Cattle, Dissertation submitted for degree of Doctor of Philosophy in Animal Science, (1999).

DeJarnette, J.M., et al., Accessory Sperm: Their Importance to Fertility and Embryo Quality, and Attempts to Alter Their Numbers in Artificially Inseminated Cattle, J. Anim Sci, (1992), 70:484-491.

Foote, R.H., The History of Artificial Insemination: Selected Notes and Notables, American Society of Animal Science, (2002), 1-10.

Furmus, et al, Effect of Hyaluronic Acid on Development of In Vitro Produced Bovine Embryos, Centro de Investigaciones Reproductivas Perez Companc, Theirogenology (1998), 49:1489-1499.

Gao, Q.H, et al., Successful Low Dose Insemination of Flow Cytometrically Sorted Sika (Cervus Nippon) Sperm in Wapiti (Cervus Elaphus), Animal Reproduction Science, (2009).

George, F., et al., Set Up of a Serum-Free Culture System for Bovine Embryos: Embryo Development and Quality Before and After Transient Transfer, Theriogenology 69, (2008), 612-623.

Graves, et al., Evaluation of Uterine Body and Bilteral Uterine Horn Insemination Techniques, J. Dairy Sci. (1991) 3454-6, 74(10).

Hawk, H.W., Transport and Fate of Spermatozoa After Insemination of Cattle, Journal of Dairy Science , (1987), pp. 1487-1503, vol. 70, No. 7.

Hawk, H.W., et al, Effect of Unilateral Cornual Insemination upon Fertilization Rate in Superovulating and Single-Ovulating Cattle, J Anim Sci, (1986), 63:551-560.

Hawk, H.W., Sperm Survival and Transport in the Female Reproductive Tract, J Dairy Sci (1983) 66:2645-2660.

Heiskanen et al., Insemination Results with Slow-Cooled Stallion Semen Stored for 70 or 80 Hours, Theriogenology (1994), 1043-1051, vol. 42., Iss. 6.

Hunter, RH; Advances in Deep Uterine Insemination: A Fruitful Way Forward to Exploit New Sperm Technologies in Cattle, Anim Reprod Sci., (2003) 157-170, 79(3-4).

Hunter et al., Deep Uterine Insemination of Cattle: A Fruitful Way Forward with Smaller Numbers of Spermatozoa, Acta Vet Scand. (1998), 149-63, 39(2.

Hunter, R.F.H., et al., Sperm Transport in the Cow: Periovulatory Redistribution of Viable Cells Within the Oviduct, Reprod. Nutr Develop., 24: (1984), 597-608.

Januskauskas, A., et al, Relationship Between Sperm Response to Glycosaminoglycans In Vitro and Non-Return Rates of Swedish Dairy AI Bulls, Reprod Dom Anim 35, (2000), 207-212.

Kurykin, et al., Fixed Time Deep Intracornual Insemination of Heifers at Synchronized Estrus, Theirogenology (2003), 1261-8; 60(7).

López-Gatius, F., et al., Intraperitoneal Insemination and Retrograde Sperm Transport in Dairy Cows, J. Vet. Med. A 47, (2000), 83-88.

Mitchell, J.R., Distribution and Retention of Spermatozoa with Acrosomal and Nuclear Abnormalities in the Cow Genital Tract, J. Amin. Sci., (1985), 61:956-967.

Munkittrick, T.W., Accessory Sperm Numbers for Cattle Inseminated with Protamine Sulfate Microcapsules, J. Dairy Sci. (1992), 75:725-731.

Nebel, et al, Microencapsulation of Bovine Spermatozoa for Use in Artificial Insemination: A Review, Reproduction, Fertility and Development (1993), 701-712, 5(6).

Nebel et al, Microencapsulation of Bovine Spermatozoa, J. Anim Sci (1985), 60:1631-1639.

(56) References Cited

OTHER PUBLICATIONS

Niżański, Wojciech, Intravaginal Insemination of Bitches with Fresh nd Frozen-Thawed Semen with Addition of Prostatic Fluid: Use of an Infusion Pipette and the Osiris Catheter, Theriogenology, (2006), 470-483, vol. 66, Iss. 2.
Palasz, A.T., et al., Effects of Hyaluronan, BSA, and Serum on Bovine Embryo In Vitro Development, Ultrastructure, and Gene Expression Patterns, Molecular Reproduction and Development (2006), 73:1503-1511.
Peippo. J. et al., Embryo Production From Superovulated Holstein-Friesian Dairy Heifers and Cows After Insemination With Frozen-Thawed Sex-Sorted X Spermatozoa or Unsorted Semen, Anim Reprod Sci. (2009), 111(1): 80-92.
Peña, F.J., et al., Effect of Hyaluronan Supplementation on Boar Sperm Motility and Membrane Lipid Architecture Status After Cryoperservation, Theriogenology 61 (2004), 63-70.
Ranganathan, Sripriya et al, Evidence for Presence of Hyaluronan Binding Protein on Spermatozoa and Its Possible Involvement in Sperm Function, Molecular Reproduction and Development (1994) 38:69-76.
Rodriguez-Martinez, H., Role of the Oviduct in Sperm Capacitation, Theriogenology 68S, (2007), S138-S146.
Saacke, R.G., et al., Involvement of the Bull and Inseminate in Fertility and Embryo Quality, AET Convention, (1994), 43-55.
Saacke, R.G., What Happens to All Those Sperm?: The Interation of Male and Female in Success of Mating, Theriogenology (2004), Lexington, KY.
Salisbury, G.W., et al., Preservation of Bovine Spermatozoa in Yolk-Citrate Diluent and Field Results From Its Use, Journal of Dairy Science, (1941), 905-910, vol. XXIV, No. 11.
Salisbury, G.W., et al., Further Studies of the Effect of Dilution Rate on the Fertility of Bull Semen Used for Artificial Insemination, (1944) 233-241.
Salisbury, G.W., Fertility of Bull Semen Diluted at 1:100, J. Dairy Sci. (1946), 695-697.
Salisbury, G.W., et al., Fertility Level of Bull Semen Diluted at 1:400 With and Without Sulfanilamide, (1948), 817-822.
Schenk, J.L., et al., Effects of Extender and Insemination Dose on Postthaw Quality and Fertility of Bovine Sperm, J Dairy Sci 70 (1987), 1458-1464.
Sieme, et al., Effects of Different Artificial Insemination Techniques and Sperm Doses on Fertility of Normal Mares and Mares with Abnormal Reproductive History, Theriogenology, (2004), 915-928, vol. 62, Iss. 5.
Sirard, M.-A, et al., In Vivo and In Vitro Effects of FSH on Oocyte Maturation and Developmental Competence, Theriogenology 68S, (2007) S71-S76.
Suarez, S.S., Interactions of Spermatozoa with the Female Reproductive Tract: Inspiration for Assisted Reproduction, Reproduction, Fertility and Development, (2007), 19, 103-110.
Talbot, Prudence, et al., Cell Adhesion and Fertilization: Steps in Oocyte Transport, Sperm-Zona Pellucida Interactions, and Sperm-Egg Fusion, Biology of Reproduction 68, (2003), 1-9.
Tanabe, T.Y., The Nature of Reproductive Failure in Cows of Low Fertility, Wisconsin Agricultrual Experiment Station, (1948), Paper No. 383, 237-246.
Tanghe, Sofie, et al., Cumulus Contributions During Bovine Fertilization In Vitro, Theriogenology 60, (2003), 135-149.
Testing Committee Report, Abstracts of Papers Presented at the Thirty-Seventh Annual Meeting, (1942), 667-731.
Van Soom, et al., Deep Intrauterine Insemination in Cattle, Gynecologie, Obstetrique & Fertilite, (2004), 32 (10): 911-5.
Vandemark, N.L., Sperm Transport in the Perfused Genital Tract of the Cow, Am. J. Physiol (1955),183: 510-512.
Verberckmoes et al., Assessment of a New Utero-Tubal Junction Insemination Device in Dairy Cattle, Theriogenology, (2004), 103-115, vol. 61, Iss. 1.
Verberckmoes et al., Low Dose Insemination in Cattle with the Ghent Device, Theirogenology, (2005) 1716-1728, vol. 64, Iss. 8.
Verberckmoes, Steven; Preservation of Fresh Bovine Semen and Utero-Tubal Junction Insemination in Cattle, de Faculteit Diergeneeskunde, Universiteit Gent (2004), Thesis.
Weeth, H.J., et al., Comparative Efficiency of Intracervical and Intra-Uterine Methods of Insemination in Dairy Cattle, Dept. of Dairy Husbandry, Missouri Agricultural Experiment Station Journal, (1950) 195-198, Series No. 1224.
Wilmut, I., et al., Sperm Transport into the Oviducts of Heifers Mated Early in Oestrus, Reprod. Nutr. Develop., (1984), 24 (4), 461-468.

* cited by examiner

ARTIFICIAL BREEDING TECHNIQUES FOR BOVINES INCLUDING SEMEN DILUENTS AND AI APPARATUS

This application is a continuation-in-part of U.S. Pat. No. 8,202,210 issued on Jun. 19, 2012 entitled "Artificial Breeding Techniques for Bovines Including Semen Diluents and AI Apparatus".

BACKGROUND OF THE INVENTION

Various artificial breeding techniques have been developed for mammals and specifically bovines, including artificial insemination ("AI") and embryo transfer ("ET").

Various breeds of cattle are often bred for specific purposes. For example, Angus, Brahman, Charolais, Hereford, Polled Hereford and Simmental are often bred for beef production. Holstein, Jersey, Guernsey, Ayrshire and Brown Swiss are often bred for the dairy industry. The following discussion is intended as background on cattle in general and this data may vary depending on the specific breed, food availability or the lack thereof and the weather.

In a natural setting, cows, heifers and at least one bull are free to roam in a pasture. The gestation for bovines is about 9½ months. After a calf is born, there is a delay of 2 or 3 months before the cow will come into heat (estrus). Heifers may have an even longer rebreeding delay. This delay in rebreeding allows the cow to produce milk for the new calf and bring hormones back to normal levels. After this delay (postpartum anestrous) the cow will usually come into heat every 18-24 days, unless interrupted by pregnancy or some problem.

Cows have two ovaries, but in the natural setting only one egg will be released from one ovary during each estrous cycle. The egg will travel down the respective oviduct. During heat, the cow is sexually attractive to both bulls and cows and will stand firm when other animals attempt to mount her. During heat, the three fibrous rings in the cow's cervix relax. Therefore when a bull mates with a cow in heat, his penis passes through the vulva, the posterior vagina, and the anterior vagina to a point very near the external cervical os. When the bull ejaculates, approximately 4-9 billion sperm are injected into the anterior vagina. Some of these sperm are transported through folds in the lining of the cervix then into the uterine horns (endometrium) of the uterus and finally into the oviducts. Conception occurs in the oviducts. The fertilized egg travels down the oviduct and embeds itself in the horn of the uterus where it develops until birth.

Conception rates for natural sexual breeding are very high because of the high number of sperm that are ejaculated per intercourse and because the bull will typically mate the cow or heifer on multiple occasions while she is in heat.

As previously mentioned, cattle are raised for a number of different purposes including dairy cattle, beef cattle, rodeo cattle, and seed cattle which are used to build a herd. The lifespan of cattle varies depending on the goals of the rancher. For example, beef cattle reach maturity in two to three years, but may be slaughtered after they reach a sufficient weight in 15-20 months. In the dairy industry, female calves from the best cows are saved for herd replacement, and bull calves are usually sold at a few days of age to be eventually slaughtered for beef. Mature dairy females are often slaughtered after 3 or 4 years of milk production. But beef seed stock cattle and rodeo cattle may have substantially longer lives to increase the number of high quality calves that are produced per cow. Left in a natural setting and well managed with adequate food and water, cattle will produce on average about one calf per year. Assuming the cow lives 10 years, and gives birth to her first calf in the second year of life, the average beef cow will produce about 7 to 8 calves over her lifespan. The average dairy cow will only produce about 2 to 3 calves in her lifetime due to the stresses of high lactation output.

To increase the value of a cow's calves beef cattle ranchers and dairymen utilize frozen semen from the most valuable bulls in the industry to breed their cows. Since frozen semen can be shipped commercially around the world, the best bulls can be mated to thousands of cows instead of the usual 20 to 40 under natural pasture mating conditions.

Cryopreservation techniques for semen are well known to those skilled in the art and will be briefly summarized. About 5 ml to about 15 ml of semen is collected from a bull using an artificial vagina. The semen is mixed with a suitable extender and cryoprotectant. Assuming about 10 ml of semen have been collected, it may be mixed with about 240 ml of TRILADYL® solution, which is an off the shelf product that is available from Minitube of America in Verona, Wis. (www.minitube.com) The Triladyl® solution contains an extender and a cryoprotectant, such as glycerol. The mixture of semen, extender and cryoprotectant is then placed in plastic straws and frozen. In the industry the contents of the frozen straw is generally referred to as frozen semen, although is also contains an extender and a cryoprotectant. The goal is to cryopreserve about 20 million motile sperm in a ½ ml semen straw.

Artificial insemination (AI) is the process whereby frozen semen is thawed, placed in a AI instrument, and manually passed through the vagina, then the cervix and ultimately into the body of the uterus where it is deposited. Only a few drops of semen is typically used per prior art AI session. Semen straws contain about ¼ or ½ ml of fluid and typically only one or two straws are used per prior art AI session. To increase the number of calves that a valuable cow can produce, embryo transfer (ET) techniques have been developed and are well know to those skilled in the art. Conventional embryo transfer techniques include injection of genetically valuable cows with suitable hormones which cause them to produce multiple eggs (oocytes) in a single estrous cycle. This process is often referred to as superovulation. Each cow is then artificially inseminated with semen from a valuable bull that has been cryopreserved using conventional cryopreservation techniques.

During superovulation, semen fertilizes some of the oocytes, which are then referred to as embryos. However, many of the eggs are not fertilized or they die shortly after fertilization. All of these unfertilized oocytes, dead embryos, and live embryos (collectively known as ova) are flushed from the cow with a liter or more of embryo flush solution (Embryo flush solution is sometimes also referred to as recovery solution, in the industry). Each live embryo that is recovered is either transferred fresh into a recipient cow or cryopreserved to be transferred later into a recipient cow. The recipient cow is a surrogate mother, used for development of the fertilized embryo, birth and rearing of the calf. The recipient cow is typically less expensive than the genetically valuable donor cow from which the embryos are harvested.

As previously mentioned, a cow in a natural setting with a life span of 10 years may produce about 7 calves over her lifetime. Using conventional procedures of embryo transfer, a donor cow with a life of 10 years may produce as many as 20 to 40 calves over her lifetime, with the help of multiple recipient cows.

AI produces conception rates of about 50 to 70% in single ovulating beef cattle, but only about 20-40% in dairy cattle. There is still room for improvement of artificial breeding techniques to improve rates of conception and therefore increase the total number of calves that a valuable donor cow can produce over her lifetime.

U.S. Pat. No. 5,147,229 to Mendoza is for a "Device to Facilitate Artificial Insemination of Bovines and Similar Animals". As shown in Mendoza '229 at FIGS. 2 and 9, the AI instrument with an expanding balloon 2 is used to anchor the tip of the artificial insemination device in the cervix to create a seal. U.S. Pat. No. 6,071,231 to Mendoza is an improvement on Mendoza '229 and is for another insemination instrument with a balloon catheter as best seen in FIGS. 4-6. In Mendoza '231, at Column 2, beginning at line 5, the device is described as follows:

> In operation, the frozen semen sample in a common plastic semen storage straw . . . is warmed and mixed with diluting fluid contained in an ampoule. The diluted semen is then loaded into the inseminating pipette by aspirating it out of the ampoule, whereupon it is pushed with air from a syringe out of the distal end of the pipette into the uterus of the animal through the anchored tip which is sealed against the cervix to prevent the fluid from leaking back.

Mendoza '231 describes the process of the second patent as follows, beginning at Column 4, line 60: "With the aid of a plastic lighted speculum 32 to open the animal's vagina and view the interior, the device 29 is pressed part way into the cervix 33, the balloon 24 is inflated to form a seal with the cervix, and the dilution fluid is forced out of the syringe, pushing the semen sample and diluent into the uterus 34." One advantage of the present artificial insemination instrument is that it does not require a lighted speculum in order to be inserted into the cow. Instead, the present AI instrument is inserted using the rectal palpation technique as described herein and as better seen in FIG. 5. It is therefore more economical to produce the present AI instrument because there is no need for the lighted speculum of Mendoza.

In Mendoza '299 and Mendoza '231, the AI instrument has a balloon type catheter used to position and seal the dispensing tip of the instrument in the cervix of the animal. The present invention does not use a catheter with a balloon, thus making is less costly to produce. Further, the dispensing tip of the present invention is either positioned at the body of the uterus or in the uterine horns, not the cervix.

In Mendoza '299, the amount of semen diluent is described as being contained in an ampoule, which is a small glass sealed vial. Mendoza '299 never discloses the amount of diluent that is in the ampoule. In Mendoza '231, the patent calls for an optimum total charge of semen and diluting fluid, but no specific amounts are ever disclosed, except that the diluting fluid is in an ampoule.

U.S. Pat. No. 7,056,279 is entitled "Device and Method for Artificial Insemination of Bovines and other Animals". The '279 patent cites Mendoza '231 and describes insemination techniques as follows beginning at column 7, line 12:

> In the classical insemination technique, the straw is thawed and opened at one side and inserted in the insemination instrument. The semen is expelled by moving the cotton plugs forward by means of a stainless steel rod. For the insemination instrument according to the invention, straws can be used. The straws are first thawed at 37° C., during one minute and then the semen (0.25 ml) is then expelled in an ampoule which contains 0.25 ml sodium citrate. The total of 0.5 ml is sufficient for a successful insemination by the deposition of 0.25 ml semen solution for each uterine horn.

The '279 patent teaches that a total of about 1.0 ml of thawed cryopreserved semen and diluent are sufficient for AI of both uterine horns. Further, the '279 patent teaches that this mixture should be deposited near the uterotubal junction (See col. 8, lines 3-8).

Applicant believes that there is still a need for improved AI procedures and apparatus. Specifically, the present invention uses substantially more insemination medium that the aforementioned prior art patents to flood the uterine horns. The present invention does not deposit the insemination medium near the uterotubal junction. Instead, the insemination medium of the present invention is deposited at the body of the uterus or at the posterior of each uterine horn.

U.S. Pat. No. 5,030,202 is for a "Lavage System" The term "lavage" means a therapeutic washing out of an organ or part. This patent applies to animals and in particular to equines (horses). Female horses (mares) sometimes have trouble conceiving immediately after giving birth (foaling). Apparently, part of the difficulty may be retained placenta or infection in the uterus. The uterine lavage apparatus 10 of FIG. 1 includes an inflatable cuff 42 (balloon) better seen in FIG. 2 which is the gravid uterus of a post partum mare. The inflatable cuff 42 is shown in the inflated position in FIG. 2. The cuff 42 is also shown in the inflated position in FIG. 2A which is the nongravid uterus of a mare. This washing technique (lavage) is particularly applicable to post partum mares and is not an artificial insemination procedure.

U.S. Pat. No. 2,566,632 is for an "Artificial Insemination Device". At column 4 line 8, the patent states: "Thus, when the syringe 13 (Referring to FIG. 1) is operated and semen is drawn into the tubing 10, it will flow into the chamber 16 . . . " "The size of the cavity or dome like chamber 16 may vary but it has been found desirable that this space or chamber have a capacity of about 1 cc. of semen, this being the proper amount for insertion in the animal." Col. 4, lines 23-27. (1 cc equals 1 ml). The semen never enters the bore of the instrument beyond the chamber 16 or the syringe. (Col. 4, lines 55-58). Thus this prior art device uses only a 1 ml dose of semen, contrary to the teaching of the present patent application which recommends that the uterine horns be flooded with insemination medium to better increase the probability of conception. This prior art device does not place the insemination medium in the syringe.

SUMMARY OF THE INVENTION

The invention includes an improved nonsurgical procedure for artificial insemination of bovines. The AI instrument used in the present invention does not use a balloon and is therefore sometimes referred to as "catheter free" or the procedure is referred to as a "catheter free" procedure. The procedure is especially useful with cows that have trouble conceiving and with large or older cows that have enlarged uterine horns. The invention may also lead to breakthroughs in the more widespread use of sex sorted sperm. In one embodiment, the improved procedure uses an insemination medium to flood the uterus with fluid in order to insure that some sperm reaches the tip of the uterine horns, which should improve conception rates. The insemination medium is a mixture of cryopreserved semen that has been thawed and a "suitable solution". The frozen semen is thawed and warmed prior to mixture with the "suitable solution", which is also warmed. In one embodiment, the insemination medium is mixed and then injected into the bovine.

In another embodiment, the "suitable solution" may be injected into the bovine in sufficient volume to flood the uterine horns followed by the semen. Some mixing may occur in the reproductive organs of the bovine. In yet another embodiment, the semen may be injected into the bovine, followed by the "suitable solution" to flood the uterine horns. Again, some mixing may occur in the reproductive organs of the bovine. However, to ensure thorough mixing of the semen and the "suitable solution", Applicant recommends that the insemination medium be mixed prior to injection into the bovine.

The invention may be used with or without superovulation. The invention includes a catheter free artificial insemination instrument which may include a syringe connected to a disposable single use pipette. (AI instruments are also sometimes referred to as insemination rods or AI guns.) The procedure for flooding the uterine horns with the insemination medium does not require use of the "suitable solutions" disclosed herein or the specific AI instrument also disclosed herein. In one embodiment, at least a portion of the pipette of the AI instrument should be inserted onto the body of the uterus to concurrently flood both the left and the right uterine horns. Concurrent flooding of both uterine horns is generally easier and faster for most clinical personnel to correctly position at least a portion of the pipette of an AI instrument in the body of the uterus, than the posterior of each uterine horn. However, it is also possible for skilled clinical personnel to practice this procedure by insertion of at least a portion of the pipette of the AI instrument into the posterior of one uterine horn to flood that horn and then reposition at least a portion of the pipette of the AI instrument into the posterior of the other uterine horn to flood it in a sequential fashion.

BRIEF DESCRIPTION OF THE DRAWINGS

The AI instrument of FIG. 3 has been inserted to the body of the uterus and the uterine horns have been flooded with insemination medium.

DETAILED DESCRIPTION OF THE INVENTION

Conventional artificial reproduction techniques may include hormone injections into the donor cow to induce superovulation with many eggs being released over several hours from both ovaries. These eggs flow into the oviduct.

In the U.S., a cryopreserved straw of semen contains about ½ ml of liquid with about 10-30 million motile sperm. Cryopreserved semen from Canada, Mexico or Europe is often stored in straws containing about ¼ ml of liquid with about 10-30 million motile sperm. These cryopreserved semen straws are kept under liquid nitrogen in tanks and will keep almost indefinitely. When it is time to artificially inseminate a cow, a straw of frozen semen is removed from a liquid nitrogen tank and warmed to about 95° F. (about 35° C.). After thawing, the straw is typically placed directly in an artificial insemination instrument.

The conventional catheter free AI instrument is an elongate metal tube with an elongate metal plunger. The od of the metal tube is about ⅛ inch (about 3 mm) and the overall length is about 18 inches (about 46 cm). The warmed straw of semen is put in the distal end of the conventional AI instrument and the exposed tip of the plastic semen straw is cut off. A plunger is located at the proximal end of the AI instrument.

The cow is restrained in a squeeze shoot or other mechanism. The AI instrument containing the thawed semen straw is then placed in a disposable elongate plastic sheath. The tip of the sheath engages the straw, forming a seal to prevent semen leaks. Sheaths of this design are well known to those skilled in the art and are produced by IMV Technologies of L'Aigle, France (www.imv-technologies.com). The conventional elongate plastic sheath is a single use disposable item. The conventional metal AI instrument is reused repeatedly. The AI instrument and the elongate plastic sheath may then be put in a chemize, which is a thin disposable plastic sleeve that fits over the elongate plastic sheath. Use of a chemize is optional in AI procedures. The chemize is more commonly used in ET procedures. (See U.S. Pat. No. 4,453,936 for a description of one type of chemize.)

Using conventional rectal palpation techniques, well known to those skilled in the art, the AI instrument, warmed straw of semen, plastic sheath and optionally a chemize are carefully inserted through the vulva, the vagina, and up to the external cervical os or opening. If a chemise is in place, the AI technician pushes the AI gun and plastic sheath through the chemize. The insemination instrument is then passed through the three fibrous rings in the cervix and into the body of the uterus. The metal plunger is then depressed which ejects the semen from the straw, and through the outlets in the plastic sheath into the body of the uterus. On some occasions, more than one semen straw may be used in a single AI session. If the semen is deposited in the proper location, some of the sperm are transported up both horns of the uterus into the oviducts to hopefully fertilize one or more of the eggs that are present. As previously mentioned, conception occurs in the oviducts. It is easy for inexperienced clinical personnel to improperly position the AI instrument in the cow's reproductive organs. In some cases, the AI procedure is unsuccessful and no eggs are fertilized. Even when successful, sometimes not all of the available eggs are fertilized for several different reasons.

Conventional AI techniques use millions of sperm per insemination whereas a bull deposits billions of sperm each time he mates with a cow or heifer. Further, the bull is not shy repeatedly mating with a cow while she is in heat, further increasing the enormous number of sperm and the large volume of semen in the reproductive system of a cow, while she is in heat. Another problem with conventional AI techniques is that some cows are thought to have poor sperm transport mechanisms. Normally, smooth muscles of the uterine horns contract and help push sperm towards the tip of the horns near the oviduct. The junction of the uterine horn and the oviduct is referred to as the uterotubal junction ("UTJ"). At the UTJ is a valve which opens spasmodically to allow a limited amount of sperm into the oviduct.

In the case of embryo transfer, embryo recovery or flushing is generally accomplished through nonsurgical techniques at approximately six to seven days after AI. The donor cow is placed in a squeeze shoot to hold it in place and an epidural block is often given at the tail head.

An embryo flush solution, such as buffered saline, will be used to recover the embryos, if any from the uterine horns. Conventional flushing techniques are typically used with prior art ET procedures and are well know to those skilled in the art, but will be briefly summarized.

A Foley type catheter is connected to a 1 or 2 liter bag of conventional embryo flush solution. A Foley type catheter has a balloon on the distal end to anchor the catheter in place. In the industry the balloon is sometimes referred to as a bladder. Foley type catheters are commonly used after surgery to drain the human bladder. However, the same apparatus is also used in cows in connection with ET techniques. The term "catheter" as used herein refers to a Foley type catheter with an inflatable balloon on the distal end. Term "catheter free" as used herein means that the AI device and/or the AI procedure of the present invention does not utilize an inflatable balloon.

Using conventional ET techniques, a Foley type catheter is carefully inserted through the vulva, the vagina and past the three fibrous rings of the cervix to the body of the uterus. The balloon of the catheter is inflated to anchor the catheter in place. A first clamp is then opened allowing conventional embryo flush solution into the horns of the uterus through the inlet of the catheter. About 20 ml to about 100 ml of embryo flush solution is allowed to flow into the horns of the uterus. The first clamp is closed and a second clamp is opened. Clinical personnel may then gently massage the horns of the uterus using conventional rectal palpation techniques to force the conventional embryo flush solution to drain through the outlet of the catheter into about a 50 micron filter (See U.S. Pat. No. 4,563,172 for example). This process of flushing and draining is repeated until about 1 liter of embryo flush solution has been circulated through the uterus. The conventional embryo flush solution passes through the filter and is discarded. The eggs and embryos, if any are collected in the filter. Conventional embryo flush solution is an off the shelf product and may be purchased from various vendors, including Bioniche Life Sciences, Inc. of Belleville, Ontario, Canada which sells its flush solution under the name "ViGro Complete Flush Solution" (www.bionicheanimalhealth.com). The collected embryos, if any and the unfertilized eggs are typically transferred to a square petri dish for visual screening under a microscope. The live embryos, if any, are then typically transferred to a smaller petri dish. The live embryos may be cryopreserved for future embryo transfer and/or the live embryos may be non-surgically transferred into a recipient cow. Other conventional flushing techniques are described in Canadian Patent 1,073,286 "Apparatus for Use in Collecting Eggs from Animals".

Figure 1:
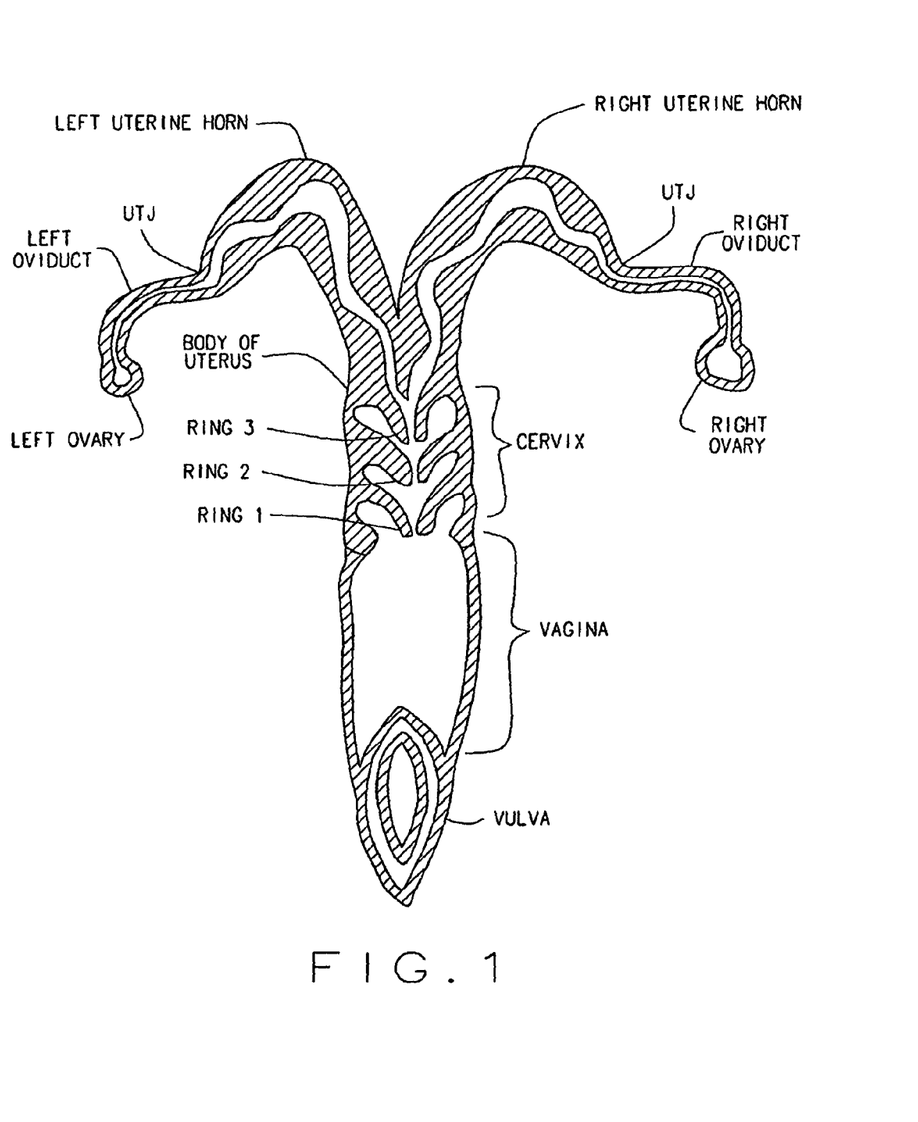
FIG. 1 is a top section view of a cow's reproductive organs.
Figure 2:
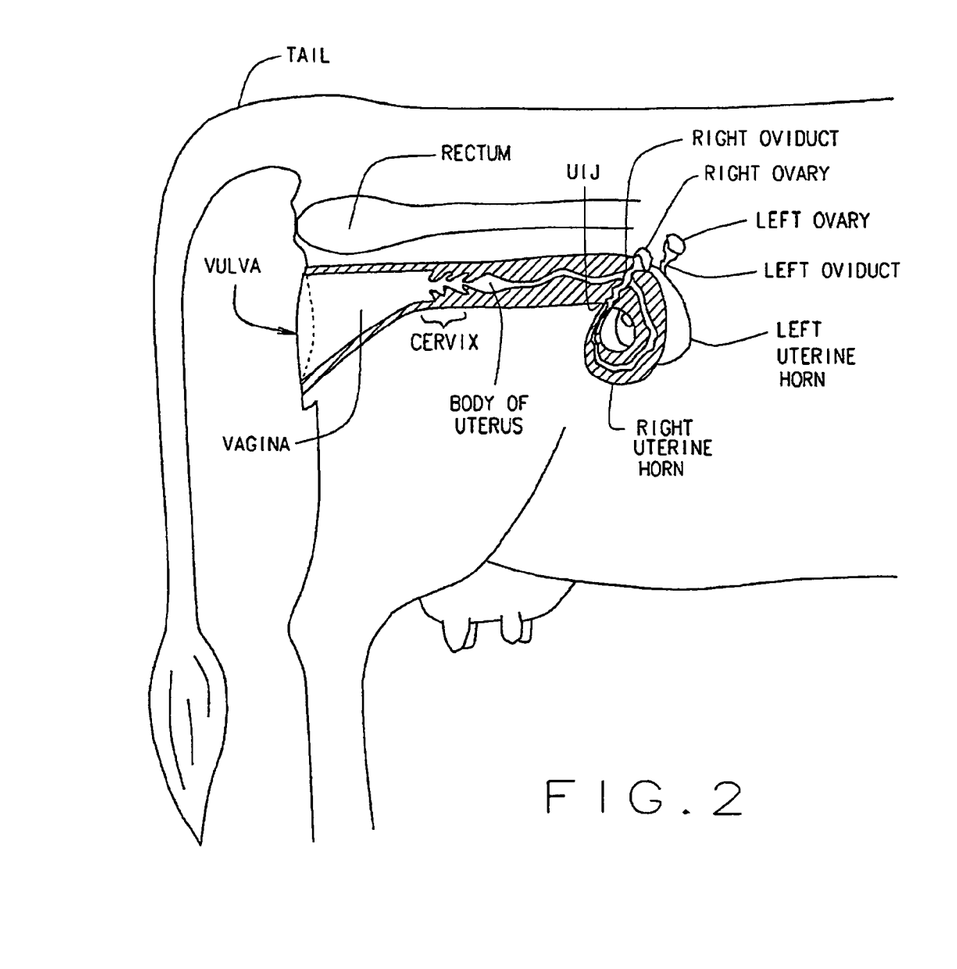
FIG. 2 is a side section view of a cow's reproductive organs.

Referring now to FIG. 1, the reproductive organs of a female bovine are shown in top section view and referring to FIG. 2, the reproductive organs are shown in side section view. The vulva is the external opening to the vagina. The cervix has three fibrous annular rings that are tightly contracted, except when the bovine is in heat. When the bovine comes into heat, the three rings relax allowing sperm easier passage into the uterus. Sperm is then deposited by a bull into the vagina and is transported through the cervix into the body of the uterus. During AI even though the three fibrous rings are relaxed it can often be difficult for clinical personnel to pass an AI instrument through the cervix and position the tip properly in the body of the uterus.

In a natural (non-superovulated) setting one egg is released from the left or right ovary and it travels down the respective oviduct. When a bull breeds a bovine in a natural setting, some of the sperm are transported up the uterine horns to the oviduct to fertilize the egg. If the egg is fertilized it lingers in the oviduct for about 4 days and then migrates into the uterine horn. The embryo begins implanting in the uterine horn about 15 days after conception.

Some prior art AI techniques deposit a quarter to a half ml of thawed cryopreserved semen in the body of the uterus. U.S. Pat. No. 7,056,279 teaches that a total of about 1.0 ml of thawed cryopreserved semen and diluent are sufficient for AI of both uterine horns. After conventional AI, the sperm must then be transported up the collapsed and convoluted uterine horns to the oviduct to hopefully fertilize one or more eggs, if the bovine has been superovulated. The number of cryopreserved sperm used in prior art AI procedures is millions compared with a bull which ejaculates billions. Further, in a natural setting, a bull ejaculates about 5-15 ml of semen per ejaculation. The AI procedure of the present invention is designed to overcome some of the limitations of prior art AI techniques by mixing the quarter or half ml of cryopreserved semen with a comparatively large amount of "suitable solution" that will keep the sperm alive and flood the uterine horns. The mixture of semen and a "suitable solution" is referred to at the insemination medium. Some prior art procedures do not mix the cryopreserved semen in the straw with any solution or diluent after the semen straw has been thawed for AI. Other prior art procedures mix the thawed cryopreserved semen with about 0.5 ml of diluent. The insemination medium, of the present invention is used in comparatively larger volumes to flood the uterine horns with motile sperm.

Figure 3:
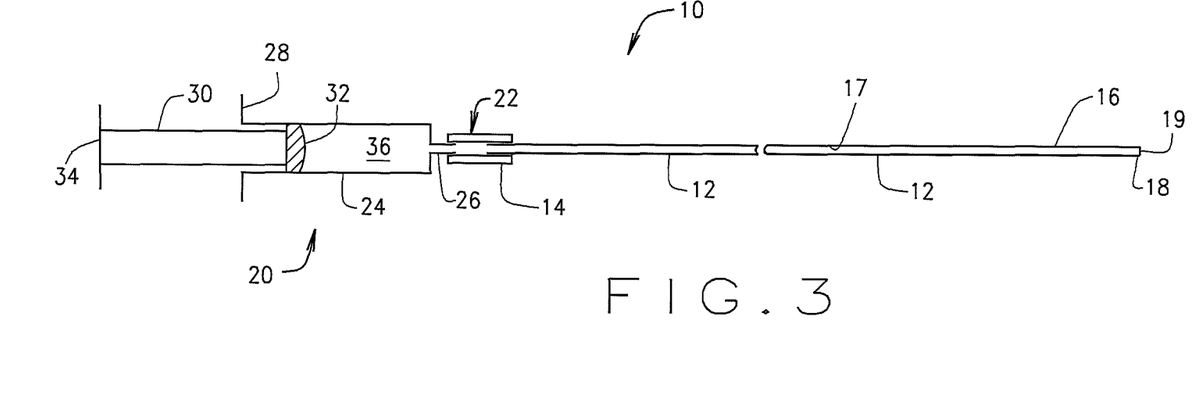
FIG. 3 is a section view of the AI instrument of the present invention.

Referring to FIG. 3, the AI instrument of the present invention is shown in section view and is generally referred to by the numeral 10. One advantage of the AI instrument of the present invention is that it does not use a balloon to anchor the instrument prior to the introduction of the insemination medium into the bovine. The AI instrument 10, which includes the pipette 12 and the pipette 122, of the present invention is sometimes referred to as "catheter free" because it does not have a balloon on the distal end. Likewise, the procedure of the present invention is sometimes referred to as a "catheter free" procedure because there is no balloon to be inflated during the procedure.

Figure 6:
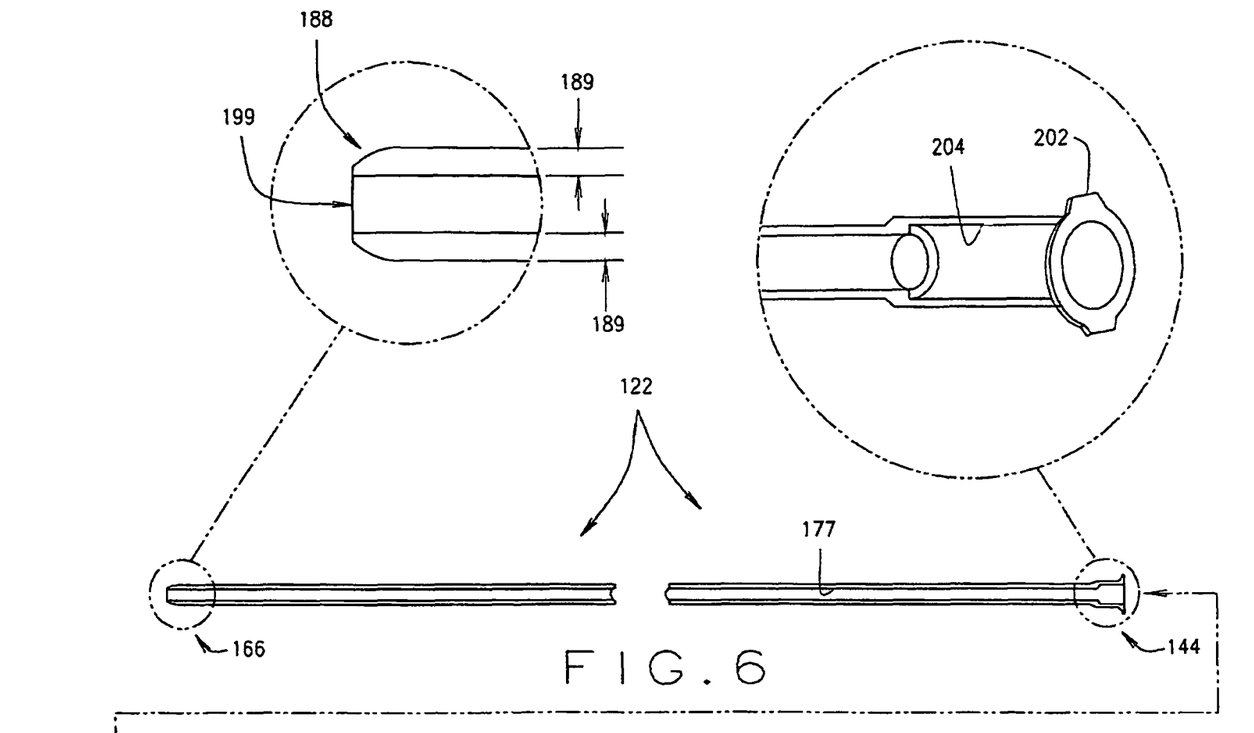
FIG. 6 is a section view of a disposable pipette that may be suitable for use in this invention.

The AI instrument 10 in FIG. 3 includes a single use disposable, hollow pipette 12 which is formed from semi-rigid plastic to facilitate insertion through the reproductive organs of a female bovine and a fluid supply reservoir. An alternative embodiment of the pipette 12 is shown in FIG. 6. The pipette shown in FIG. 3 has a proximal end 14 and a distal end 16. The pipette is about 18 inches (47.5 cm) to about 20 inches (50.8 cm) long. For older larger cows, a pipette of 22 inches (50.8) may even be appropriate. The internal diameter of the elongate passageway 17 may be about 0.2 cm and the outside diameter of the pipette may be about 0.4 cm. However, the exact dimensions of the AI instrument are not critical to this invention. The AI instrument should be long enough to pass through the bovine reproductive organs to at least the body of the uterus and preferably be able to hold a sufficient volume of insemination medium to flood the uterine horns. The distal end 16 has a smooth rounded tip 18 surrounding the outlet 19 to avoid damage to the bovine when the pipette is inserted into the reproductive organs.

A syringe 20 is connected to the pipette 12 by a connector 22. The syringe may also be generally referred to as a fluid supply reservoir that holds a sufficient volume of insemination medium to flood the uterine horns. Other fluid supply reservoirs, know to those skilled in the art, such as a squeeze bulb, are within the scope of this invention, provided that they can hold a sufficient volume of insemination medium to flood the horns of the uterus of the cow in question. The connector 22 may be a separate member. In the alternative, the connector 22 may be formed as a part of the pipette or the syringe. The syringe includes a cylindrical body 24 with a dispensing tip 26 on one end and finger tabs 28 on the other end. A piston 30 is sized and arranged to slide in the cylindrical syringe body 24. On one end of the piston is an elastomeric circular seal 32 and on the other end is a thumb tab 34. The circular seal, the cylindrical body and the dispensing tip define a solution chamber 36 holding at least a sufficient volume of insemination medium for the cow in question. The solution chamber 36 is in fluid communication with the elongate passageway 17 of the pipette 12.

In FIG. 3, the insemination medium has been drawn into the solution chamber 36 of the syringe. When the thumb tab 34 is depressed, the seal 32 slides down the syringe body 24 towards the dispensing tip 26. This pumping action forces the insemination medium through the connector 22, through the elongate passageway 17 of the pipette and out the outlet 19.

Figure 4:
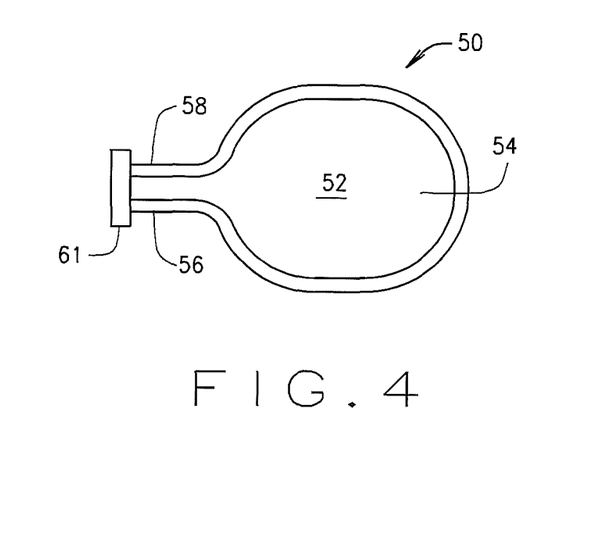
FIG. 4 is a section view of a disposable plastic bag for a "suitable solution".

FIG. 4 is a section view of a disposable plastic bag 50 for a "suitable solution". The bag 50 defines a solution chamber 52 which holds the "suitable solution" 54. The bag 50 may be prepackaged with a "suitable solution" in amounts of 5 ml, 15 ml, 30 ml and 50 ml for reasons described below. The bag further defines an outlet 56 with an outlet port 58. The outlet port 58 may be sealed with a cap 61 or it may be sealed with a needle septum, not shown, for penetration with a needle. Another alternative is a spike port, not shown. The dispensing tip 26 of the syringe 20 may be sized and arranged to engage the outlet port 58 to facilitate filling of the solution chamber of the syringe with "suitable solution" from the bag 50. The dispensing tip may alternatively be fitted with a connector such as a luer lock, not shown, to connect the syringe to a needle. The type of solution connection between the bag 50 and the syringe 20 is not critical to the practice of this invention, provided that the connection does not leak.

The size of uterine horns varies from relatively small horns in a virgin heifer to large uterine horns in older cows that have produced several calves. As a general rule, cows weighing less than 1000 pounds (453 kg) will have small uterine horns. Insemination medium in the range of from about 2 ml to about 100 ml and preferably from about 10 ml to about 20 ml and more preferably about 15 ml should do a good job of flooding the uterine horns and is a fertility enhancing amount for cows weighing less than 1000 pounds (453 kg). In some virgin heifers, a sufficient volume of insemination medium may be as little as about 2 ml to about 20 ml an preferably about 10 ml. Applicant recommends using larger volumes, but smaller volumes are also within the scope of this invention.

As a general rule, cows weighing from about 1000 (453 kg) to about 1,400 pounds (635 kg) will have medium sized uterine horns. Insemination medium in the range of from about 2 ml to about 100 ml and preferably from about 20 ml to about 40 ml and more preferably about 30 ml should do a good job of flooding the uterine horns and is a fertility enhancing amount for cows weighing from about 1000 pounds (453 kg) to about 1,400 pounds (635 kg).

As a general rule, cows weighing more than about 1,400 pounds (635 kg) will typically have larger uterine horns and be older dairy and beef cattle. Insemination medium in the range of from about 2 ml to about 100 ml and preferably from about 40 ml to about 60 ml and more preferably about 50 ml should do a good job of flooding the uterine horns and is a fertility enhancing amount for cows weighing more than about 1,400 pounds (635 kg).

As previously mentioned, the insemination medium is a mixture of a) cryopreserved semen that has been thawed and b) a "suitable solution". The following may be used as a "suitable solution" for use in the practice of this invention including: buffered saline, various commercially available embryo flush solutions, various commercially available extenders commonly used in cryopreversation of semen and other products or other solutions not identified herein may also prove useful provided they have a proper pH, osmolarity and are properly buffered to dilute and support the life of the sperm. The pH of a "suitable solution" is about 7 to about 7.4 and the osmolarity is about 280 to about 300 mOsm/L.

Various commercially available embryo flush solutions that may be suitable in the practice of this invention including:

a) Syngro Holding Medium, Vigro Complete Flush Solution, Vigro Holding Plus, Vigro Rinsing Solution all available from Bioniche Animal Health of Belleville, Ontario, Canada, (www.bionicheanimalhealtyh.com).

b) emP3 Complete Flush and emP3 Holding Solution both available from Partnar Animal Health of Port Huron, Mich., (www.partnaranimalhealth.com).

c) Emcare Complete Ultra Flush Medium, available from ICPbio International Ltd. Of Auckland, New Zealand, (www.icpbio.com).

Some extenders used in cryopreservation of bull semen may be a "suitable solution" for the practice of this invention and others may not. The term semen extender and semen diluent are sometimes used interchangeably in the industry. For example, the tris-fructose-citric acid solution listed below may be a suitable solution for the practice of this invention:

3.187 grams tris (trishydroxymethylaminomethane)
1.781 grams citric acid
1.136 grams fructose
80 ml distilled water The pH of this tris-fructose-citric acid solution is about 7 to about 7.2 and the osmolarity is about 285 mOsmi/L.

TRILADYL®, a common extender used in cryopreservation of bull semen is not a suitable solution for use in the practice of this invention because it also contains the cryoprotectant glycerol which is toxic at some concentrations to sperm at temperatures that support cell function. The semen extender disclosed in U.S. Pat. No. 6,368,786 (assigned to IMV Technologies) also contains glycerol which means that it is likewise not suitable for use in this invention. Other semen extenders such as BILADYL®, Fraction A, also from Minitube, does not contain a cryoprotectant or glycerol and may be a "suitable solution" for use in the practice of this invention.

As previously mentioned, a "suitable solution" may be conveniently premixed in volumes of 10 ml, 15 ml, 30 ml, 50 ml, and other desirable amounts and thereafter may easily be contacted with the semen to prepare the insemination medium. The amount of insemination medium may depend on the size of the uterine horns of the bovine that is being artificially inseminated. A sufficient volume of insemination medium may be used to flood both uterine horns. The uterine horns may be flooded concurrently, which is the preferred procedure or sequentially depending on the experience level of the AI technician. Both procedures are within the scope of this invention. The volume of insemination medium can be estimated from the general body size of the cow and/or rectal palpation of the horns prior to injection of the insemination medium. The term "sufficient volume" of insemination medium may also be referred to as an "effective amount" or a "fertility enhancing amount".

Figure 5:
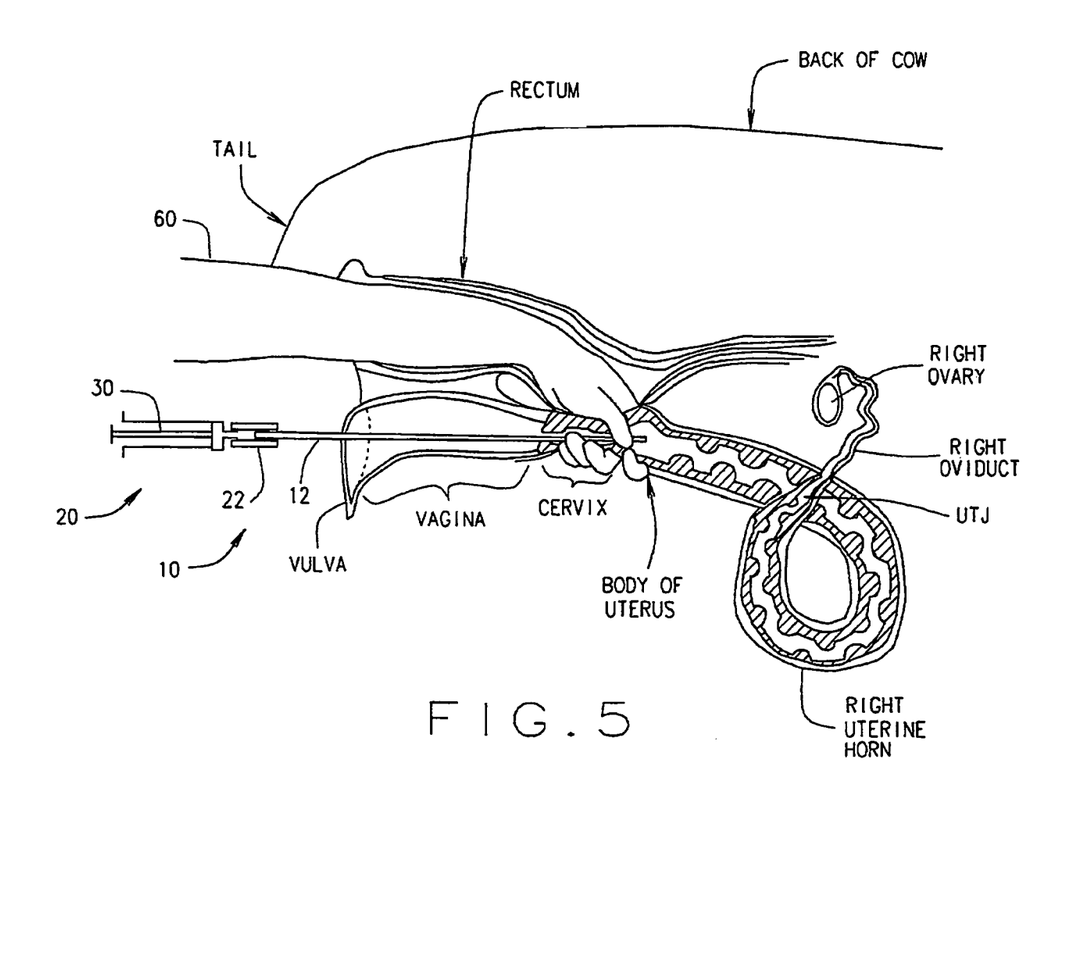
FIG. 5 is a side section view of a cow's reproductive organs showing only the right uterine horn. A person's arm is inserted into the rectum for rectal palpation of the reproductive organs.

The artificial breeding procedure of the present invention will now be described with regards to FIG. 5. At least one straw of cryopreserved semen is warmed to a suitable temperature, about 95° F. (35° C.). And preferably, a plastic bag of "suitable solution" is likewise warmed to a suitable temperature, which is also about 95° F. (35° C.). The warmed semen from the straw and the warmed "suitable solution" are mixed together forming an insemination medium. Which is drawn into the solution chamber 36 of a syringe 20 or other suitable fluid supply reservoir of an artificial insemination instrument. The empty seman straw is discarded. Another type of suitable supply resevoir is a fluid holding container that may be connected to a fluid pump. The disposable pipette 12 is removed from a delivery bag, not shown, and connected to the connector 22. The insemination medium is pumped to the orifice 19 in the pipette. One arm 60 of a person is inserted into the rectum of the bovine for rectal palpation of the bovine'reproductive organs. Specifically, the hand used to palpate the cervix to carefully guide the AI instrument through the three fibrous rings of the cervix.

The AI instrument 10 of FIG. 3 is gently inserted through the vulva, the vagina, and the cervix, to the body of the uterus in order to concurrently flood both uterine horns. As shown in FIG. 2, the uterine horns are normally in a generally flat, condition in the body of the bovine presenting a convoluted physical organ for the sperm to traverse. In contrast, in FIG. 5, the right uterine horn and the left uterine horn, not shown, have been concurrently flooded making it much easier for the sperm to be mechanically transported to the UTJ near the oviduct. In FIG. 5, the size of the uterine horns has been exaggerated and enlarged in the drawing for illustrative purposes.

In the alternative, each uterine horn may be sequentially flooded with insemination medium. To sequentially flood each horn, the tip 18 of the pipette should be inserted into the horn, slightly beyond the body of the uterus. This position is not shown in the drawings. The right uterine horn is flooded first, and then the pipette is relocated to the left uterine horn. Additional insemination medium is injected to flood the left uterine horn, not shown. The AI instrument and the pipette are then removed. Or the left horn may be flooded first and then the right horn. The order of the sequence is not important. Sequential flooding of each uterine horn is believed to be slower and more difficult than concurrent flooding, because the pipette must be relocated from one horn to the next. However, cows with an extremely short uterine body may benefit more from sequential horn flooding to insure that the insemination medium reaches both horns, which could increase conception rates. Both concurrent and sequential flooding are within the scope of this invention.

Some prior art techniques use only ¼ to ½ ml of cryopreserved semen for artificial insemination which is only a small amount of fluid (Only a few drops). Other prior art techniques as taught in U.S. Pat. No. 7,056,279 mix ¼ ml of cryopreserved semen with about ¼ ml of diluent per uterine horn. Accordingly, the prior art technique in U.S. Pat. No. 7,056,279 injects ½ ml of semen and ½ mil of diluent for a total of 1 ml of insemination medium into the bovine. In contrast, the present invention uses a large volume of insemination medium to flood the horns of the uterus. For example, in the case of sex sorted sperm for a virgin heifer, preferably about 5 ml of a "suitable solution" is mixed with ¼ ml of cryopreserved sex sorted semen, which is about 10 times more solution than some prior art AI techniques. In the case of non-sex sorted sperm for cows that have given birth to their first calf, preferably about 10 ml of suitable solution is mixed with ½ ml of cryopreserved semen, which is about 20 times more solution than some prior art AI techniques. This invention makes it easier for the sperm to be mechanically transported through the uterine horns to the UTJ, thus improving conception rates, especially in cows with larger reproductive tracts, lactating dairy cows, subfertile cows, cows being inseminated with sex sorted semen, cows being inseminated with low motility semen, superovulated cows and for cows being inseminated by inexperienced AI technicians who may not be placing semen in the precise location.

The "suitable solutions" disclosed herein are recommended for the practice of this invention but any biologically suitable solution, not disclosed herein may be used with this procedure to flood the horns of the uterus with an insemination medium, thus making it easier for the sperm to reach the UTJ and the oviduct. This procedure may be practiced with any solution that is compatible with the sperm. Further, this procedure may be used with any AI instrument and pipette that facilitates proper placement and discharge of the insemination medium to flood the uterine horns, either concurrently or sequentially.

A first alternative procedure for practice of this invention is described below. A "suitable solution" is first injected into the body of the uterus in a sufficient volume to flood the uterine horns. Then one or more thawed straws of semen are injected into the body of the uterus to mix with a "suitable solution" inside the reproductive organs of the cow. In the alternative, one or more thawed straws of semen could be injected into the body of the uterus followed by injection of a "suitable solution" in sufficient volume to flood the uterine horns. It is preferred to mix the semen with a "suitable solution" prior to injection into the cow, but this alternative procedure may also increase conception rates and be a suitable in the practice of this invention.

A second alternative procedure for practice of this invention is described below. A "suitable solution" is first injected into one horn of the uterus in a sufficient volume to flood that uterine horn. Then one or more thawed straws of semen are injected into the aforementioned uterine horn to mix with a "suitable solution" inside the reproductive organs of the cow. A "suitable solution" is injected into the opposite horn of the uterus in sufficient volume to flood that uterine horn. Then one or more thawed straws of semen are injected into the opposite uterine horn to mix with a "suitable solution" inside the reproductive organs of the cow. Again, it is preferred to mix the semen with a "suitable solution" prior to injection into the cow, but this alternative procedure may also increase conception rates.

The sex of mammals is determined by the chromosomes in the sperm, not the egg. Various segments of the cattle industry have recently found that it is valuable to use sex sorted sperm for AI in order to predetermine the sex of offspring. The sex of sperm is sorted in the dairy cattle industry to insure that a larger percentage of females will be born considering that males will not produce milk. The sex of sperm is sorted in the beef cattle industry because males better utilize feed and ultimately put on more weight than females.

Producers of sex sorted sperm currently recommend that it only be used to artificially inseminate virgin heifers, and not mature cows. This recommendation is based on at least two reasons. First, the uterine horns of virgin heifers are small making the physical transportation of inseminated sperm from the uterus to the oviduct more likely with only a ¼ ml straw of semen. Second there are only about 2 million sex sorted sperm packaged in a ¼ ml straw of semen, compared with 20-30 million sperm in a non-sex sorted ½ ml straw of semen. This self imposed industry wide recommendation to use sex sorted sperm on virgin heifers drastically limits the market for sex sorted sperm. Applicant believes that the present invention using the aforementioned AI flooding technique will allow sex sorted semen to be used with cows in general, and not just virgin heifers. This may dramatically increase the market for sex sorted sperm in the cattle industry. The term semen as used herein includes both unsorted sperm and sex sorted sperm. The term sex sorted sperm as used herein is limited to sex sorted sperm.

FIG. 6 is a section of a disposable pipette 122 that may be suitable for use in this invention. The hollow pipette 122 is formed from semirigid plastic to facilitate insertion through the reproductive organs of a female bovine. The hollow pipette is a single use disposable product that should be relatively inexpensive. As can be seen from FIG. 6, the hollow pipette does not contain a semen straw which makes the disposable pipette 122 easier and cheaper to manufacture. The pipette 122 has a proximal end 144 and a distal end 166. The pipette is from about 18 inches (47.5 cm) to about 20 inches (50.8 cm) long. For older larger cows, a pipette of 22 inches (50.8 ) may even be appropriate. The internal diameter of the elongate passageway 177 may be about 2 mm, the outside wall 189 may be about 1 mm thick all the way around and the outside diameter of the pipette may be about 4 mm. In another embodiment, the internal diameter of the elongate passageway 177 may be about 1.5 mm and the will thickness may be about 1.25 mm to increase the rigidity of this embodiment. This outside diameter for both of these embodiments is about 4 mm. However, the exact dimensions of this AI pipette are not critical to this invention. The pipette 122 connects to a fluid supply reservoir, such as a syringe, not shown. In combination, the fluid supply reservoir and the pipette should be long enough to pass through the bovine reproductive organs to at least the body of the uterus and preferably be able to hold a sufficient volume of insemination medium to flood the uterine horns. The insemination medium is a mixture of semen from a semen straw and a suitable solution. The distal end 166 has a smooth rounded tip 188 surrounding the outlet 199 to avoid damage to the bovine when the pipette is inserted into the reproductive organs. The proximate end, 144 includes a female Luer lock connector 202 to engage a Luer lock connector on a conventional syringe, not shown. The conventional syringe is a single use disposable product that is relatively inexpensive. An interior chamber 204 is formed in the proximal end 144 of the pipette and is sized and arranged to receive the tip of a conventional syringe, not shown. In combination, the pipette 122 and a conventional syringe, not shown form a disposable, single use AI instrument that may be suitable for use in this invention.

Figure 7:
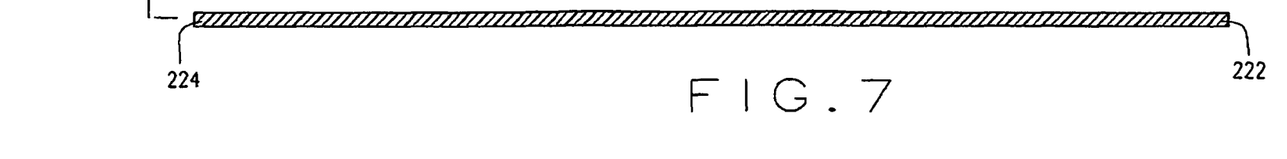
FIG. 7 is a section view of a rod used to stiffen the pipette of FIG. 6 during insertion through the cervix of a cow.

FIG. 7 is a section view of a strengthening member 220 used to further stiffen the semirigid pipette 122 of FIG. 6 during insertion through the cervix of a cow. The strengthening member may also be referred to as the rod 220. The rod 220 may be inserted in the pipette 122 of FIG. 6 to stiffen the pipette prior to insertion of the pipette and the rod through the cervix of a cow. The rod 220 may be solid, as shown and may be formed from any suitable plastic or metal. The rod may be a disposable single use product or it may be reused, if properly sterilized. In the alternative, the rod may be a hollow cylinder closed on both ends, not shown, or a hollow cylinder open on both ends, not shown. The rod 220 should have a outside diameter that is sized and arranged so the rod will easily slide in and out of the elongate passageway 177 of the pipette 122. The rod 220 may be an inch or two longer than the pipette 122, so the handle 222 of the rod 220 will protrude beyond the luer lock 202 to allow the rod 220 to be easily withdrawn from the pipette 122 after positioning the pipette in the cervix and before injection of insemination fluid through the hollow pipette 122. Preferably, the tip 224 of the rod 220 does not protrude beyond the tip 188 of the pipette during insertion of the pipette and the rod through the cervix. A stop, not shown, may be positioned on the rod 220 to prevent accidental insertion of the rod through the pipette during insertion through the cervix, to prevent unintentional damage to the cervix. The handle 222 may include a T-shaped handle, not shown, a ball, not shown, or simply an enlarged outside diameter of the tail, not shown, may be suitable for use as a handle.

What is claimed is:

1. An instrument for artificial insemination of female bovines having uterine horns, the instrument comprising:
   a single fluid supply reservoir capable of holding from about 2 ml to about 100 ml of insemination medium;
   a one piece disposable, semirigid, plastic pipette being catheter free and having a proximal end, a distal end, and a longitudinal axis extending along its length;
   a connector for connecting the single fluid supply reservoir and the one piece disposable, semirigid, plastic pipette, the pipette being free of any sheath located therewithin;
   said pipette having a constant diameter from said connector to its distal end and consisting of having only a single outlet located at the distal end on its longitudinal axis for allowing the insemination medium to discharge therefrom;
   the fluid supply reservoir being in fluid communication with the disposable, semirigid, plastic pipette to allow the insemination medium to be pumped from the fluid supply reservoir, through the disposable, semirigid, plastic pipette to substantially flood the uterine horns; and
   the instrument for artificial insemination being free of a semen straw and a plastic lighted speculum.

2. The instrument for artificial insemination of female bovines having uterine horns of claim 1, wherein the female bovines are virgin heifers, and the single fluid supply reservoir is capable of holding from about 2 ml to about 20 ml of insemination medium.

3. The instrument for artificial insemination of female bovines having uterine horns of claim 2, wherein the female bovines are virgin heifers, and the single fluid supply reservoir is capable of holding about 10 ml of insemination medium.

4. The instrument for artificial insemination of female bovines having uterine horns of claim 1, wherein the female bovines weigh less than about 1000 pounds (453 kg), and the single fluid supply reservoir is capable of holding from about 10ml to about 20 ml of insemination medium.

5. The instrument for artificial insemination of female bovines having uterine horns of claim 4, wherein the female bovines weigh less than about 1000 pounds (453 kg), and the single fluid supply reservoir is capable of holding about 15 ml of insemination medium.

6. The instrument for artificial insemination of female bovines having uterine horns of claim 1, wherein the female bovines weigh from about 1000pounds (453 kg) to about 1,400 pounds (635 kg), and the single fluid supply reservoir is capable of holding from about 20 ml to about 40 ml of insemination medium.

7. The instrument for artificial insemination of female bovines having uterine horns of claim 6, wherein the female bovines weigh from about 1000pounds (453 kg) to about 1,400 pounds (635 kg), and the single fluid supply reservoir is capable of about 30 ml of insemination medium.

8. The instrument for artificial insemination of female bovines having uterine horns of claim 1, wherein the female bovines weigh more than about 1,400 pounds (635 kg), and the single fluid supply reservoir is capable of holding from about 40ml to about 60 ml of insemination medium.

9. The instrument for artificial insemination of female bovines having uterine horns of claim 8, wherein the female bovines weigh more than about 1,400 pounds (635 kg), and the single fluid supply reservoir is capable of holding about 50 ml of insemination medium.

10. An instrument for artificial insemination of female bovines having uterine horns, the instrument comprising:
  a single syringe capable of holding at least 10 ml of insemination medium;
  a single elongate, disposable, single use, one piece, semirigid, hollow, non-metallic pipette having a longitudinal axis and proximal and distal ends, the pipette defining a passageway from the proximal to the distal end, the elongate, disposable, single use, semirigid, hollow, non-metallic pipette being removably attachable to the single syringe, said pipette having a constant outer diameter and being of a length that is sufficient to pass through at least the body of the uterus of the bovine to allow the deposit of insemination medium to the uterine horn from outside the bovine;
  a connector for connecting the single syringe and the elongate, disposable, single use, one piece, semirigid, hollow, non-metallic pipette, the pipette bring free of any sheath located therewithin;
  the elongate, disposable, single use, one piece, semirigid, hollow, non-metallic pipette having an outside diameter of about 0.4 cm and being catheter free and free of any sheath located therein or therearound;
  the distal end of the elongate, disposable, single use, one piece, semirigid, hollow, non- metallic pipette being smooth and consisting of having only a single outlet located at the distal end of the pipette on its longitudinal axis for allowing the insemination medium to exit therefrom; and
  the artificial insemination instrument being free of a semen straw and a plastic lighted speculum, the insemination medium traveling solely through the pipette to the uterine horns.

11. An instrument for artificial insemination of female bovines having uterine horns, the instrument comprising:
  a single syringe having a Luer lock connector, the single syringe being capable of holding an insemination medium;
  a one piece elongate, disposable, single use, semirigid, hollow, non-metallic pipette being catheter free and free of any components located therein, the pipette having a longitudinal axis and proximal and distal ends, the pipette defining a passageway from the proximal to the distal end for the insemination medium to pass therethrough, the pipette being removably attachable to the syringe and having a constant outer diameter;
  the distal end of the one piece, elongate, disposable, single use, semirigid, hollow, non-metallic pipette being smooth and consisting of having only a single outlet located at the distal end of the pipette on its longitudinal axis for allowing the insemination medium to be dispensed therefrom;
  the proximal end of the elongate, disposable, single use, semirigid, hollow, non-metallic pipette having a female Luer lock connector sized and arranged to engage the Luer lock connector on the single syringe;
  the instrument for artificial insemination being free from a semen straw and a plastic lighted speculum; and
  a disposable strengthening member sized and arranged to slip into the passageway of the elongate, disposable, single use, semirigid, hollow, non-metallic pipette and to further increase the rigidity of the pipette during insertion into the bovine, the strengthening member being removable from the pipette after proper placement in the bovine and wherein the strengthening member is longer than the pipette and extends beyond the female Luer lock connector to allow removal of the strengthening member from the pipette.

* * * * *